United States Patent
Emgenbroich et al.

(10) Patent No.: US 11,426,359 B2
(45) Date of Patent: *Aug. 30, 2022

(54) METHOD FOR ADJUSTING THE RELEASE OF ACTIVE AGENT IN A TRANSDERMAL DELIVERY SYSTEM

(71) Applicant: LTS Lohmann Therapie-Systeme AG, Andernach (DE)

(72) Inventors: Marco Emgenbroich, Rheinbach (DE); Johannes Josef Leonhard, Bendorf (DE); Hans-Michael Wolff, Monheim (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/312,542

(22) PCT Filed: May 20, 2015

(86) PCT No.: PCT/EP2015/061109
§ 371 (c)(1),
(2) Date: Nov. 18, 2016

(87) PCT Pub. No.: WO2015/177209
PCT Pub. Date: Nov. 26, 2015

(65) Prior Publication Data
US 2017/0079932 A1 Mar. 23, 2017

(30) Foreign Application Priority Data
May 20, 2014 (EP) .................................... 14169026

(51) Int. Cl.
*A61K 9/70* (2006.01)
*A61K 9/00* (2006.01)
(Continued)

(52) U.S. Cl.
CPC .......... *A61K 9/7084* (2013.01); *A61K 9/0014* (2013.01); *A61K 9/7061* (2013.01);
(Continued)

(58) Field of Classification Search
None
See application file for complete search history.

(56) References Cited

U.S. PATENT DOCUMENTS

| | | | |
|---|---|---|---|
| 4,769,028 A | 9/1988 | Hoffman et al. | |
| 4,814,168 A | 3/1989 | Sablotsky et al. | |

(Continued)

FOREIGN PATENT DOCUMENTS

| CA | 2374930 A1 | 1/2001 |
|---|---|---|
| CN | 1462185 A | 12/2003 |

(Continued)

OTHER PUBLICATIONS

International Search Reportissued in corresponding International Application No. PCT/EP2015/061109.
(Continued)

*Primary Examiner* — Isis A Ghali
(74) *Attorney, Agent, or Firm* — ProPat, LLC; Cathy R. Moore

(57) ABSTRACT

The present invention relates to the use of an additive in a transdermal therapeutic system with an active agent-containing layer in the form of a biphasic layer having a hydrophilic inner phase and a hydrophobic outer phase, in which the inner phase includes the additive and an active agent dissolved therein. The additive has a higher affinity to water than to the active agent and controls the permeation rate of the active agent in a manner which is independent from its concentration in the biphasic layer, with the maintenance of the permeation rate being proportional to the amount of active agent in the biphasic layer.

14 Claims, 1 Drawing Sheet

(51) Int. Cl.
*A61K 31/381* (2006.01)
*A61K 47/32* (2006.01)

(52) U.S. Cl.
CPC .......... *A61K 9/7069* (2013.01); *A61K 31/381* (2013.01); *A61K 47/32* (2013.01)

(56) References Cited

U.S. PATENT DOCUMENTS

| | | | |
|---|---|---|---|
| 4,994,267 | A | 2/1991 | Sablotsky |
| 4,994,278 | A | 2/1991 | Sablotsky |
| 5,032,207 | A | 7/1991 | Sablotsky et al. |
| 5,300,291 | A | 4/1994 | Sablotsky et al. |
| 5,405,486 | A | 4/1995 | Sablotsky et al. |
| 5,474,783 | A | 12/1995 | Miranda et al. |
| 5,656,285 | A | 8/1997 | Sablotsky et al. |
| 5,656,286 | A | 8/1997 | Miranda et al. |
| 5,686,099 | A | 11/1997 | Sablotsky et al. |
| 5,719,197 | A | 2/1998 | Kanios et al. |
| 5,958,446 | A | 9/1999 | Miranda et al. |
| 6,024,976 | A | 2/2000 | Miranda et al. |
| 6,221,383 | B1 | 4/2001 | Miranda et al. |
| 6,235,306 | B1 | 5/2001 | Miranda et al. |
| 6,884,434 | B1 | 4/2005 | Müller et al. |
| 7,383,083 | B2 | 6/2008 | Fischer et al. |
| 7,847,014 | B2 | 12/2010 | Koch et al. |
| 8,211,462 | B2 | 7/2012 | Breitenbach et al. |
| 8,246,979 | B2 | 8/2012 | Schacht et al. |
| 9,265,752 | B2 | 2/2016 | Wang et al. |
| 2001/0053383 | A1 | 12/2001 | Miranda et al. |
| 2003/0026830 | A1 | 2/2003 | Lauterback et al. |
| 2003/0060479 | A1 | 3/2003 | Brown et al. |
| 2003/0149394 | A1 | 8/2003 | Joshi |
| 2003/0198622 | A1 | 10/2003 | Van Osdol et al. |
| 2004/0131897 | A1 | 7/2004 | Jenson et al. |
| 2004/0137045 | A1* | 7/2004 | Breitenbach ......... A61K 9/7069 424/449 |
| 2004/0138299 | A1 | 7/2004 | Cahill et al. |
| 2004/0234583 | A1 | 11/2004 | Müller |
| 2005/0019385 | A1 | 1/2005 | Houze |
| 2005/0175678 | A1 | 8/2005 | Breitenbach |
| 2005/0202073 | A1* | 9/2005 | Jackson ............... A61K 9/7053 424/449 |
| 2005/0260254 | A1 | 11/2005 | Breitenbach et al. |
| 2006/0263419 | A1 | 11/2006 | Wolff |
| 2009/0048556 | A1 | 2/2009 | Durand |
| 2009/0299304 | A1 | 12/2009 | Tang |
| 2010/0119585 | A1 | 5/2010 | Hille et al. |
| 2010/0286590 | A1 | 11/2010 | Durand |
| 2010/0311661 | A1 | 12/2010 | Kullertz |
| 2011/0027345 | A1 | 2/2011 | Wang et al. |
| 2011/0104244 | A1 | 5/2011 | Hille et al. |
| 2014/0046279 | A1 | 2/2014 | Leonhard et al. |
| 2015/0290142 | A1 | 10/2015 | Cawello et al. |

FOREIGN PATENT DOCUMENTS

| | | |
|---|---|---|
| CN | 1606435 A | 4/2005 |
| CN | 1671375 A | 9/2005 |
| CN | 1897935 A | 1/2007 |
| CN | 101146524 A | 3/2008 |
| CN | 101601664 A | 12/2009 |
| CN | 102458397 A | 5/2012 |
| CN | 102770128 A | 11/2012 |
| DE | 10 2012 013 421 | 1/2014 |
| EP | 1 669 063 A1 | 6/2006 |
| EP | 2 177 217 A1 | 4/2010 |
| EP | 2 292 219 A1 | 3/2011 |
| JP | 1998509621 A | 9/1998 |
| JP | 2003-526656 A | 9/2003 |
| JP | 2004-521085 A | 7/2004 |
| JP | 2004-525164 A | 8/2004 |
| JP | 2004-528359 A | 9/2004 |
| JP | 2005-528425 A | 9/2005 |
| JP | 2005-535686 A | 11/2005 |
| JP | 2005535687 A | 11/2005 |
| JP | 2006515952 A | 6/2006 |
| JP | 2006178807 A | 7/2006 |
| JP | 2007-528392 A | 10/2007 |
| JP | 2009297808 A | 12/2009 |
| JP | 2010-106037 A | 5/2010 |
| JP | 2010158554 A | 7/2010 |
| JP | 2010536434 A | 12/2010 |
| JP | 2011-500647 A | 1/2011 |
| JP | 2011-504902 A | 2/2011 |
| JP | 2011-526592 A | 10/2011 |
| JP | 2012501799 A | 1/2012 |
| JP | 2012-504609 A | 2/2012 |
| JP | 2012-509276 A | 4/2012 |
| JP | 2006508908 A | 3/2013 |
| JP | 2013510805 A | 3/2013 |
| JP | 2013515041 A | 5/2013 |
| WO | WO 89/10108 | 11/1989 |
| WO | WO 91/14463 | 10/1991 |
| WO | WO 92/19451 | 11/1992 |
| WO | WO 93/00058 | 1/1993 |
| WO | WO 95/18603 | 7/1995 |
| WO | 89/49582 A2 | 9/1999 |
| WO | 1999/049852 A1 | 10/1999 |
| WO | 2000/44437 A1 | 8/2000 |
| WO | 2001/01967 A1 | 1/2001 |
| WO | 2002/015903 A2 | 2/2002 |
| WO | 2002/089777 A1 | 11/2002 |
| WO | 2003/015678 A1 | 2/2003 |
| WO | 2003/092677 A1 | 11/2003 |
| WO | 2004/012721 A2 | 2/2004 |
| WO | WO 2004/012730 | 2/2004 |
| WO | 2004/050083 A1 | 6/2004 |
| WO | 2005/00924 A1 | 1/2005 |
| WO | 2005/009424 A | 2/2005 |
| WO | 2005/063236 A1 | 7/2005 |
| WO | 2005/063237 A1 | 7/2005 |
| WO | 2005/092331 A1 | 10/2005 |
| WO | 2005/119610 A1 | 12/2005 |
| WO | 2008/061639 A1 | 5/2008 |
| WO | 2009/068520 A2 | 6/2009 |
| WO | 2010/042152 A2 | 4/2010 |
| WO | WO 2011/076879 | 6/2011 |
| WO | WO-2011057714 A3 * | 7/2011 .......... A61K 9/7007 |
| WO | 2012/071175 A1 | 5/2012 |
| WO | WO 2012/084969 | 6/2012 |
| WO | 2013/075823 A1 | 5/2013 |
| WO | WO 2013075822 | 5/2013 |
| WO | 2013/088254 A1 | 6/2013 |
| WO | 2014/079573 A1 | 5/2014 |
| WO | 2014/195352 A1 | 12/2014 |

OTHER PUBLICATIONS

Office Actions in U.S. Appl. No. 14/443,210, dated Nov. 28, 2016; May 4, 2017; Dec. 11, 2017; Oct. 16, 2018; and Mar. 18, 2019.
Office Actions in U.S. Appl. No. 16/009,613, dated Mar. 24, 2017 and Oct. 5, 2017. (parent to U.S. Appl. No. 16/009,613).
Office Actions in U.S. Appl. No. 15/312,433, dated Jul. 18, 2019.
Office Actions in U.S. Appl. No. 15/312,509, dated Jan. 16, 2018; Jul. 27, 2018; and Jul. 11, 2019.
Office Actions in U.S. Appl. No. 16/009,613, dated Dec. 20, 2018.
International Preliminary Report on Patentability, PCT/EP2013/003515, which corresponds to U.S. Appl. No. 14/443,210, filed May 15, 2015.
International Search Report, PCT/EP2013/003515, which corresponds to U.S. Appl. No. 14/443,210, filed May 15, 2015.
Dow Corning: Amine-Compatible Silicone Adhesives, Jul. 28, 2008.
Henkel Corporation, "DURO-TAK and GELVA Transdermal Pressure Sensitive Adhesives," Product Selection Guide, Sep. 2013.
H.F. Hammond in D. Satas "Handbook of Pressure Sensitive Adhesive Techology" (1989) 2nd ed., Chapter 4, Van Nostrand Reinhold, New York, p. 38.

(56) References Cited

OTHER PUBLICATIONS

Kandavilli, Sateesh et al., "Polymers in Transdermal Drug Delivery Systems," Pharmaceutical Technology, May 2002, pp. 62-80.
Fachinformation Neupro (Aug. 2011) with English Translation. Www.ucb.com/investors/Our-equity-story/Neupro(Jan. 6, 2016).
"Pressure Sensitive Tack of Adhesives Using an Inverted Probe Machine" ASTM D2979-71 (1982).
K.L. Ulman and R.P. Sweet, "The Correlation of Tape Properties and Rheology" (1998), Information Brochure, Dow Corning Corp., USA.
Chinese Search Report for the CN Application 201380054953.X, which corresponds to U.S. Appl. No. 14/443,210, filed May 15, 2015.
Dow Corning 360 Medical Fluid, (retrieved from on-line website; https://www.b2bcomposites.com/msds/ted/71115.pdf, pp. 1-7, 2010).
Chien, Yie W., "Transdermal Controlled Systemic Medications" pp. 36-45 (Marcel Dekker, Inc. 1987).
International Search Report, PCT/EP2015/061112, which corresponds to U.S. Appl. No. 15/312,433, filed Nov. 18, 2016.
Chien, "Developmental Concepts and Practice in Transdermal Therapeutic Systems," Chapter 2 in Transdermal Controlled Systemic Medications, 1987, vol. 31, pp. 25-44.
JP Application No. 2018-147720 First Office Action, which corresponds to U.S. Appl. No. 16/009,613.
JP Application No. 2016-522618 First Office Action, which corresponds to U.S. Appl. No. 16/009,613.
JP Application No. 2016-522618 Second Office Action, which corresponds to U.S. Appl. No. 16/009,613.
Office Actions in U.S. Appl. No. 14/443,210, dated Nov. 21, 2019 and Jul. 21, 2020.
Office Actions in U.S. Appl. No. 15/312,433, dated Mar. 23, 2020 and Oct. 21, 2020.
Office Actions in U.S. Appl. No. 15/312,509, dated Apr. 15, 2020.
Office Actions in U.S. Appl. No. 16/009,613, dated Nov. 7, 2019 and May 22, 2020.
International Preliminary Report on Patentability, PCT/EP2014/064166, which corresponds to U.S. Appl. No. 14/975,478, filed Dec. 18, 2015.
International Search Report, PCT/EP2015/061099, which corresponds to U.S. Appl. No. 15/312,509, filed Nov. 18, 2016.

* cited by examiner

METHOD FOR ADJUSTING THE RELEASE OF ACTIVE AGENT IN A TRANSDERMAL DELIVERY SYSTEM

CROSS REFERENCE TO RELATED APPLICATIONS

The present application claims priority to International Patent Application No. PCT/EP2015/061109 filed on May 20, 2015, which claims priority from European Patent Application No. 14169026.3 filed on May 20, 2014. Both International Patent Application No. PCT/EP2015/061109 and European Patent Application No. 14169026.3 are hereby incorporated herein in their entirety.

TECHNICAL FIELD OF THE INVENTION

The present invention relates to the use of an additive for the control of the permeation rate of the active agent in a transdermal therapeutic system (TTS) and a corresponding method of adjusting the period of permeation of a transdermal therapeutic system.

BACKGROUND OF THE INVENTION

Transdermal therapeutic systems are designed to provide constant dosing of the active agent across the skin and into the bloodstream during the administration period. TTS thus require less frequent dosing and provide constant blood levels during the dosing period avoiding fluctuating blood levels in danger of either being associated with increased side effects or insufficient treatment. Useful dosing periods range from 1 day to 7 days, whereas 7 days are in particular attractive due to the convenient weekly exchange schedule. On the other hand, it is technically challenging to provide TTS with constant release rates for time periods as needed and in particular for long periods of time as a 7 days period. A concentration dependent release relying on the concentration gradient between the TTS and the blood stream has limits in terms of dosing intervals and needs a large amount of active in the TTS in excess of the active actually permeating and thus being administered and which is only present tor providing the driving force for diffusion. It is thus advantageous to have a mechanism of release which is independent of the concentration of the active in the TTS and thus has the ability to provide the total amount of active in the TTS for administration and which allows the tailoring of the period of administration by the total amount of active in the TTS.

OBJECTS AND SUMMARY OF THE INVENTION

It is an object of the present invention to provide a system for the control of the release of an active agent from a transdermal therapeutic system which is independent from the active agent concentration.

It is an object of the present invention to provide a system for the control of the release of an active agent from a transdermal therapeutic system which allows the adjusting of the period of administration by adjusting the amount of active in the TTS.

It is an object of the present invention to provide a system for the control of the release of active agent from a transdermal therapeutic system which makes use of the total amount of active in the TTS.

This object is accomplished by the present invention, which relates to the use of an additive in a transdermal therapeutic system with an active agent-containing layer in the form of a biphasic layer having a hydrophilic inner phase and a hydrophobic outer phase, wherein the inner phase comprises the additive and an active agent dissolved therein, wherein the additive has a higher affinity to water than to the active agent, for the control of the permeation rate of the active agent in a manner which is independent from its concentration in the biphasic layer, wherein the maintenance of a permeation rate is proportional to the amount of active agent in the biphasic layer.

This object is also accomplished by the present invention, which relates to a method of adjusting the period of permeation of a transdermal therapeutic system by
  providing a transdermal therapeutic system with an active agent-containing layer in the form of a biphasic layer having a hydrophilic inner phase and a hydrophobic outer phase,
  wherein the inner phase comprises the additive and an active agent dissolved therein, wherein the additive has a higher affinity to water than to the active agent,
  adjusting the amount of active in the inner phase of the biphasic layer to the desired administration period.

Without wishing to be bound to any theory, it is believed that the additive which forms a solution with the active agent and has a higher affinity to water than to the active agent takes up cutaneous water during application of the TTS to the skin of a patient and thereby displacing dissolved active agent. The displaced molecules of active agent are subject to a high driving force for the diffusion out of the TTS to the skin and into the skin. The diffusion and thereby the permeation rate of the active agent is thus independent from the concentration of active agent in the TTS and is maintained over the desired administration period in accordance with the total amount of active agent in the TTS.

In accordance with the invention, the permeation rate is determined by an in vitro permeation test performed over an extended period of time using a 51 µm thick membrane consisting of an ethylene vinyl acetate (EVA) copolymer with 9% vinyl acetate (COTRAN™ Membrane, 3M) and the Paddle over Disk apparatus described in the United States Pharmacopeia (USP), Phosphate buffer pH 4.5 was used as acceptor medium (900 ml; 32° C.; 50 rpm). The permeation rate of the active agent into the acceptor medium was determined in regular intervals using a validated UV photometric or HPLC method, determination by HPLC is preferred. In accordance with the invention, the permeation rate is independent from the concentration of active agent in the biphasic system of the TTS. That is, the permeation rate provided by the TTS according to the invention does not change significantly, i.e., is constant within 20% points, preferably within 15% points, more preferably within 10% points, when the concentration of active agent in the biphasic layer is amended, e.g., within a range of the active agent concentration from 1% to 30%, preferably from 1% to 26%, Additionally, the maintenance of a permeation rate of a certain TTS is proportional to the amount of active agent in the biphasic layer. That is, for the provision of a sufficient and continuous permeation rate of active agent over several days, a corresponding higher amount of active agent in $mg/cm^2$ is required than for a TTS designed for a 1-day administration of active agent. According to the invention, the maintenance of a permeation rate of active agent is proportional within 20% points, preferably within 15% points, more preferably within 10% points to the amount of active agent in the biphasic layer.

Within the meaning of this invention, the parameter "permeation of the active agent" is provided in µg/cm² and relates to the amount of active agent permeated at a certain elapsed time within the total time period of permeation as measured in an in vitro permeation test. The value is a mean value of at least 3 experiments.

Within the meaning of this invention, the parameter "permeation rate" is provided in µg/cm²/hr and is calculated from the amount of active agent permeating during a certain sample interval, e.g., from hour 8 to hour 12, as measured through an EVA membrane in µg/cm², divided by the hours of said sample interval, e.g., 4 hours.

In accordance with the invention, the skin permeation rate is determined by an in vitro permeation test performed over an extended period of time using dermatomized human skin of about 300 µm thickness in a flow cell setup. A phosphate buffered saline (PBS) pH 6.2 was used as acceptor medium (32° C.). The permeation rate of the active agent into the acceptor medium was determined in regular intervals using a validated UV photometric or HPLC method, determination by HPLC is preferred. In accordance with the invention, the skin permeation rate is independent from the concentration of active agent in the biphasic system of the TTS. That is, the permeation rate provided by the TTS according to the invention does not change significantly, i.e., is constant within 20% points, preferably within 15% points, more preferably within 10% points, when the concentration of active agent in the biphasic layer is amended, e.g., within a range of the active agent concentration from 1% to 30%, preferably from 1% to 26%. Additionally, the maintenance of a skin permeation rate of a certain TTS is proportional to the amount of active agent in the biphasic layer. That is, for the provision of a sufficient and continuous skin permeation rate of active agent over several days, a corresponding higher amount of active agent in mg/cm is required than for a TTS designed for a 1-day administration of active agent. According to the invention, the maintenance of a skin permeation rate of active agent is proportional within 20% points, preferably within 15% points, more preferably within 10% points to the amount of active agent in the biphasic layer.

Within the meaning of this invention, the parameter "skin permeation of the active agent" is provided in µg/cm² and relates to the amount of active agent permeated at a certain elapsed time within the total time period of permeation as measured in an in vitro skin permeation test. The value is a mean value of at least 3 experiments.

Within the meaning of this invention, the parameter "skin permeation rate" is provided in µg/cm²/hr and is calculated from the amount of active agent permeating during a certain sample interval, e.g., from hour 9 to hour 12, as measured through skin in µg/cm², divided by the hours of said sample interval, e.g., 3 hours.

Within the meaning of this invention, the term "transdermal therapeutic system" (or TTS) refers to a system by which the active agent is administered systemically and in particular refers to the entire individual unit that is applied to the skin of a patient, and which comprises an effective amount of the active agent in a self-adhesive layer structure and optionally an additional larger active-free self-adhesive layer structure (overlaying adhesive) on top of the active agent-containing self-adhesive layer structure. During storage, such a TTS is normally located on a detachable protective layer from which it is removed immediately before application to the surface of the patient's skin. A TTS protected this way may be stored in a blister pack or a side sealed bag.

Within the meaning of this invention, the term "active agent-containing self-adhesive layer structure" refers to the active agent-containing structure providing the area of release of the active agent during administration. The overlaying adhesive adds to the overall size of the TTS but docs not add to the area of release. The active agent-containing self-adhesive layer structure comprises a backing layer, an active agent-containing biphasic layer and optionally an additional skin contact layer.

Within the meaning of this invention, the term "biphasic" refers to a system of two distinguishable, e.g., visually distinguishable, areas, an outer phase and an inner phase, wherein the inner phase is in form of dispersed deposits within the outer phase. Such deposits are e.g., solid solution deposits. Deposits that are visually distinguishable may be identified by use of a microscope Within the meaning of this invention, the term "biphasic layer" refers to the final biphasic layer solidified after coating the coating mixture by e.g. drying a solvent-containing coating mixture or cooling a hot-melt coating mixture. Solvent-containing coating mixtures are preferred according to the invention. The biphasic layer may also be manufactured by laminating two or more layers (e.g. dried layers) of the same composition to provide the desired area weight.

Within the meaning of this invention, the term "dried biphasic layer" refers to a biphasic layer obtained from a solvent-containing coating mixture after coating on a film and evaporating the solvents (solvent-based layer) and is to be distinguished from a biphasic layer obtained from a hot-melt coating mixture (hot-melt-based layer).

Within the meaning of this invention, the term "log P" is dimensionless and refers to the logarithm of the octanol/water partition coefficient which is defined as the ratio of the solubility concentration of a compound in octanol (a non-polar solvent) to its solubility concentration in water (a polar solvent). The higher the partition coefficient, the more non-polar the compound. Log P values are generally inversely related to aqueous solubility and known as a measure of lipophilicity. The octanol/water partitioning coefficients (octan-1-ol/water partitioning coefficients) are determined at pH 7.4, 37° C. and an ionic strength of 0.15 in an appropriate buffer solution according to the method described by E. Miyamoto et al. (E. Miyamoto et al. "Physico-chemical Properties of Oxybutynin" Analyst (1994), 119, 1489-1492).

Within the meaning of this invention, the term "hygroscopic" is the ability of a substance to absorb water.

The TTS according to the invention is manufactured with starting materials containing a minimum amount of water.

Within the meaning of this invention, the term "solid solution" refers to a mixture of active agent and the additive to provide a single homogeneous phase in form of a solid-state solution.

Within the meaning of this invention, the terms "polymer mixture" includes mixtures of polymers comprising the same monomer(s) but providing different grades. Polymers of different grades are polymers which are distinguishable by different properties (e.g. the viscosity) and are usually commercially available under different trademarks. E.g., the commercially available products KOLLIDON® 90 and KOLLIDON® 30 provide individual grades of polyvinylpyrrolidone, a polymer of the monomer vinylpyrrolidone; the commercially available products DOW CORNING® BIO PSA 7-4201 and BIO PSA 7-4301 provide individual grades of pressure-sensitive adhesive polysiloxane.

Within the meaning of this invention, the term "pressure-sensitive adhesive composition" refers to a composition that in particular adheres with finger pressure, is permanently tacky, exerts a strong holding force and should be removable from smooth surface without leaving a residue. The pressure-sensitive adhesive properties of the pressure-sensitive adhesive composition are based on suitable tackifiers, or on a polymer or polymer mixture which is a/are pressure-sensitive adhesive polymer(s), or on both. Pressure-sensitive adhesive polymer(s) are available in solid form or in a mixture with a suitable solvent (e.g. heptanes or ethyl acetate). According to a certain embodiment, the polymer or polymer mixture is a/are pressure-sensitive adhesive polysiloxane(s). Examples of useful pressure-sensitive adhesive polysiloxanes which are commercially available include the standard BIO-PSA series (7-4400, 7-4500 and 7-4600 series), the amine compatible (endcapped) BIO-PSA series (7-4100, 7-4200 and 7-4300 series), the Soft Skin Adhesives series (7-9800), and the BIO-PSA Hot Melt Adhesives manufactured by Dow Corning. Preferred pressure-sensitive polysiloxanes are heptane- and ethyl acetate-solvated pressure-sensitive adhesive polysiloxanes including BIO-PSA 7-4201, BIO-PSA 7-4301, BIO-PSA 7-4202, and BIO-PSA 7-4302.

Within the meaning of this invention, the term "pressure-sensitive adhesive mixture" refers to a pressure-sensitive adhesive polymer or pressure-sensitive adhesive polymers at least in mixture with a solvent (e.g., heptanes or ethyl acetate).

Within the meaning of this invention, the term "polyvinylpyrrolidone" refers to polyvinylpyrrolidone which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include KOLLIDON® 12 PF, KOLLIEDON® 17 PF, KOLLIDON® 25, KOLLIDON® 30 and KOLLIDON® 90 F supplied by BASF. The different grades of KOLLIDON® are defined in terms of the K-Value reflecting the average molecular weight of the polyvinylpyrrolidone grades. KOLLIDON® 12 PF is characterized by a K-Value range of 10.2 to 13.8, corresponding to a nominal K-Value of 12. KOLLIDON® 17 PF is characterized by a K-Value range of 15.3 to 18.4, corresponding to a nominal K-Value of 17. KOLLIDON® 25 is characterized by a K-Value range of 22.5 to 27.0, corresponding to a nominal K-Value of 25, KOLLIDON® 30 is characterized by a K-Value range of 27.0 to 324, corresponding to a nominal K-Value of 30. KOLLIDON® 90 F is characterized by a K-Value range of 81.0 to 97.2, corresponding to a nominal 20 K-Value of 90. Preferred KOLLIDON® grades are KOLLIDON® 30 and KOLLIDON® 90 F.

Within the meaning of this invention, the term "K-Value" refers to a value calculated from the relative viscosity of polyvinylpyrrolidone in water according to the European Pharmacopoeia (Ph.Eur.) and USP monographs for "Povidone".

Within the meaning of this invention, the term "area weight" refers to the dry weight of an individual layer or the sum of individual layers, except backing layer and release liner, and is provided in g/m². The area weight may be the coating weight of a layer, or the sum of the coating weights of individual layers. Amounts of active agent or polymer in a layer provided in mg/cm² or % refer to or are based on the area weight of the layer.

If not indicated otherwise "%" refers to weight-%.

DETAILED DESCRIPTION

Figure 1:
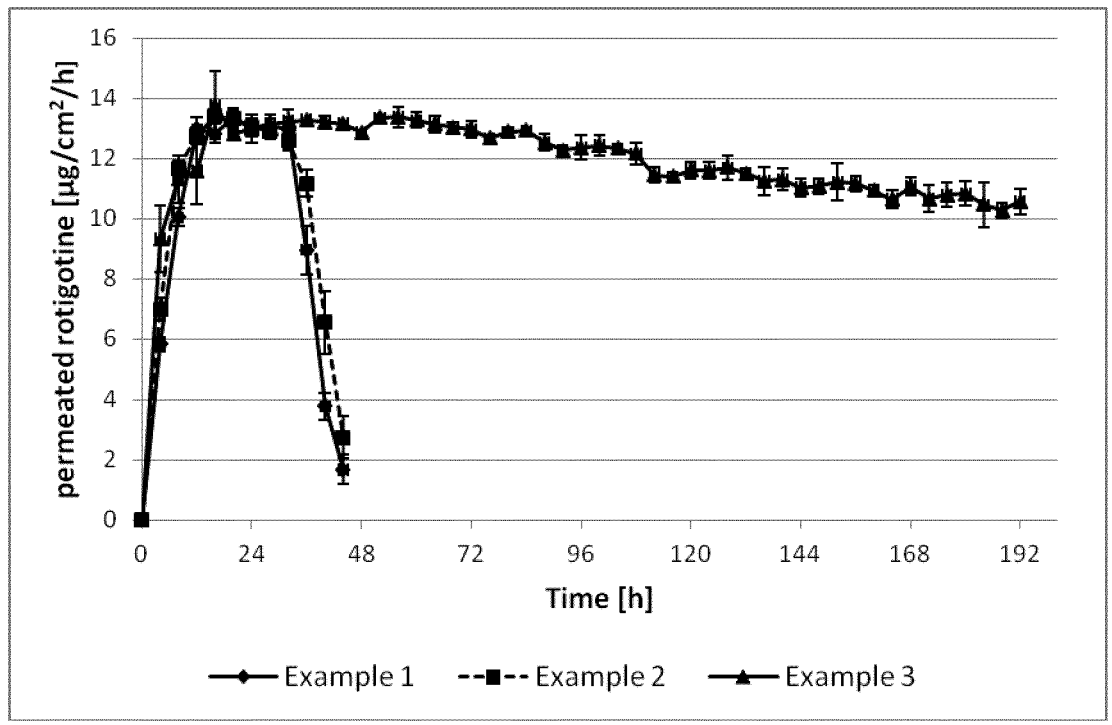
FIG. 1 depicts the permeation rate of Example 1, Example 2 and Example 3.

In accordance with the invention, the additive is used in a transdermal therapeutic system with an active agent-containing layer in the form of a biphasic layer having a hydrophilic inner phase and a hydrophobic outer phase, wherein the inner phase comprises the additive and an active agent dissolved therein,
  wherein the additive has a higher affinity to water than to the active agent, for the control of the permeation rate of the active agent in a manner which is independent from its concentration in the biphasic layer, wherein the maintenance of a permeation rate is proportional to the amount of active agent in the biphasic layer.

In accordance with the invention, there is a method of adjusting the period of permeation of a transdermal therapeutic system by
  providing a transdermal therapeutic system with an active agent-containing layer in the form of a biphasic layer having a hydrophilic inner phase and a hydrophobic outer phase,
  wherein the inner phase comprises
  the additive and an active agent dissolved therein,
  wherein the additive has a higher affinity to water than to the active agent,
  adjusting the amount of active in the inner phase of the biphasic layer to the desired administration period.

According to the invention, the additive forms a solid solution with the active agent.

The additive in accordance with the invention may be a hygroscopic composition. According to certain embodiments, the additive is a hygroscopic polymer or a mixture of hygroscopic polymers. The hygroscopic polymer or the mixture of hygroscopic polymers may be able to take up water from about 1% up to about 60%, preferably from about 10% up to about 60%, more preferably from about 30% up to about 60%.

According to certain embodiments, the additive is a hygroscopic polymer or a mixture of hygroscopic polymers selected from the group consisting of:
  polyvinylpyrrolidones,
  copolymers of vinyl caprolactam, vinylacetate and ethylene glycol,
  copolymers of vinylpyrrolidone and vinylacetate,
  copolymers of ethylene and vinylacetate,
  polyethylene glycols,
  polypropylene glycols,
  acrylic polymers,
  modified celluloses.

According to certain specific embodiments, the additive is a hygroscopic polymer or a mixture of hygroscopic polymers selected from the group consisting of:
  polyvinylpyrrolidones having a K-Value of at least 80, or from 80 to 200,
  polyvinylpyrrolidones having a K-Value of less than 80, or from 10 to 79, copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
copolymers of dimethylaminoethyl methacrylate, butyl methacrylate and methyl methacrylate,
copolymers of methacrylic acid and methyl methacrylate,
hydroxypropyl methylcellulose, hydroxypropyl methylcellulose acetate succinates.

According to certain embodiments, the additive is a polyvinylpyrrolidone having a K-Value of at least 80, or from 80 to 200, or a mixture of polyvinylpyrrolidone having a K-Value of at least 80, or from 80 to 200, and polyvinylpyrrolidone having a K-Value of less than 80, or from 10 to 79.

According to a certain embodiment the additive is not solely a polyvinylpyrrolidone, in particular a PVP having a K value of at least 80, or from 80 to 200.

According to certain embodiments, the amount of the additive ranges from 0.1 mg/cm$^2$ to 10.0 mg/cm$^2$, or from 0.1 mg/cm$^2$ to 5.0 mg/cm$^2$, or from 0.3 mg/cm$^2$ to 3.0 mg/cm$^2$ of the biphasic layer. The additive may be present in the biphasic layer in a concentration of about 1% to about 20%, or of about 1% to about 15%, of about 1% to about 10%.

Useful active agents for the TTS according to the invention may have a log P value of about 2.8 to about 6, or of about 3 to about 6, preferably of more than 3 to about 6, or of more than 3 to about 5.

According to certain embodiments, the active agent has a water solubility of about 1 mg/L to less than 100 mg/L, or of about 5 mg/L to about 50 mg/L, or of about 5 mg/L to about 25 mg/L, preferably the active agent has a log P value of more than 3 to about 6 and a water solubility of about 5 mg/L to about 50 mg/L.

In a preferred embodiment the active agent is an amine functional drug, which has a log P value of about 2.8 at pH. 7,4. In another preferred embodiment the amine functional drug has a pKa of 7.4 to 8.4. In an especially preferred embodiment the amine functional drug has a log P value of about 2.8 at pH 7.4 and a pKa of 7.4 to 8.4. The pKa value can be measured by standard methods. A particularly preferred method is potentiometric titration of aqueous drug solutions (without addition of organic cosolvents) at room temperature.

Particularly preferred amine functional drugs are dopamine D2 agonists, which are useful for example in the treatment of Parkinson's disease. Especially preferred dopamine D2 receptor agonists are aminotetraline compounds, such as 5,6,7,8-tetrahydro-6-[propyl-[2-(2-thienyl)ethyl]amino-1-naphthalenol (INN: rotigotine).

Other examples for particularly preferred amine functional drugs are Nphenyl-N-[1-(2-phenylethyl)-4-piperidinyl]-propanamide (INN: fentanyl) which is useful in the treatment of pain and anticholinergic drugs exerting an antispasmodic effect on smooth muscles and inhibiting the muscarinic action of acetylcholin on smooth muscles. Examples of such anticholinergic drugs which are useful in the present invention are 4-diethylamino-2-butynyl phenylcyclohexylglycolate (INN: oxybutynine) and 2-[3-(diisopropylamino)-1-phenylpropyl]-4-(hydroxymethyl) phenyl isobutyrate (INN: fesoterodine). Oxybutynine and fesoterodine are useful in the treatment of urinary incontinence. It will be understood by a person skilled in the art that the amine functional drugs, such as rotigotine, fentanyl, oxybutynine and fesoterodine, may all exist in various isomeric forms. It has to be understood that in this case the amine functional drug may be any single isomer or a mixture of different isomers. If the amine functional group contains asymmetric carbon atoms, any single enantiomer or a mixture of enantiomers may be used. Rotigotine, fentanyl oxybutynine and fesoterodine all contain one asymmetric carbon atom. Hence, the S or R-enantiomer or the racemate or any other enantiomer mixture of these compounds may be used as the amine functional drug.

According to certain embodiments of the invention, the active agent is selected from the consisting of rotigotine, fentanyl, oxybutynine, and fesoterodine.

According to a certain embodiment the active agent is not rotigotine base.

According to a certain specific embodiment the additive is not solely polyvinylpyrrolidone, in particular a PVP having a K value of at least 80, or from 80 to 200, and the active agent is not rotigotine base.

According to certain embodiments, the ratio of active agent to the additive is 1:0.2 to 1:1, preferably 1:0.2 to 1:08, or 1:0.4 to 1:0.6.

In accordance with the invention, the active agent may be present in any concentration in the biphasic layer of the TTS. According to certain embodiments, the active agent is present in a concentration of about 1% to about 30%, preferably of about 2% to about 25%, or of about 5% to about 25% of the biphasic layer.

According to certain embodiments, the active agent is present in an amount of 0.1 mg/cm$^2$ to 10.0 mg/cm$^2$ of the biphasic layer, preferably in an amount of 0.3 mg/cm$^2$ to 1.0 mg/cm$^2$, or 1.0 mg/cm$^2$ to 1.5 mg/cm$^2$, or 1.5 mg/cm$^2$ to 5.0 mg/cm$^2$.

The biphasic layer of the TTS according to the invention contains a hydrophobic outer and a hydrophilic inner phase. According to a certain preferred embodiment, the hydrophilic inner phase forms dispersed deposits in the outer phase.

The biphasic layer may be coated at any area weight, but is preferably coated at an area weight of about 30 g/m$^2$ to about 400 g/m$^2$, or of about 30 g/m$^2$ to about 200 g/m$^2$, or of about 100 g/m$^2$ to about 200 g/m$^2$.

According to certain embodiments, the biphasic layer is manufactured having a hydrophilic inner phase containing 90% to 100%, preferably 95% to 100%, or 99% to 100% of a solution consisting of said additive and the active agent.

According to certain embodiments, the biphasic layer is a dried biphasic layer. The dried biphasic layer is obtained from a solvent-containing biphasic coating mixture after coating on a film and evaporating the solvents. The obtained layer (solvent-based layer) is to be distinguished from a biphasic layer obtained from a hot-melt coating mixture (hot melt-based layer).

The biphasic layer of the TTS according to the invention may further comprise one or more anti-oxidants. Suitable anti-oxidants are sodium metabisulfite, ascorbyl palmitate, tocopherol and esters thereof, ascorbic acid, butylhydroxytoluene, butylhydroxyanisole or propyl gallate, preferably sodium metabisulfite, ascorbyl palmitate and tocopherol. The anti-oxidants may be conveniently present in an amount of from about 0.001 to about 0.5% of the biphasic layer.

The biphasic layer according to the invention may further comprise in addition to the above mentioned ingredients other various excipients or additives, for example from the group of solubilizers, fillers, tackifiers, substances which influence the barrier properties of the stratum corneum in the sense of increasing the active agent permeability, pH regulators, and preservatives. Suitable permeation enhancers may be selected from the group of fatty alcohols, fatty acids, fatty acid esters, fatty acid amides, glycerol or its fatty acid esters, N-methylpyrrolidone, terpenes such as limonene, [alpha]-pinene, [alpha]-terpineol, carvone, carveol, limonene oxide, pinene oxide, 1,8-eucalyptol and most preferably ascorbyl palmitate. In a preferred embodiment, the TTS according to the invention does not contain a penetration enhancer.

In accordance with the invention, the outer phase of the biphasic layer of the TTS is a hydrophobic outer phase. According to a certain embodiment of the invention, the hydrophobic outer phase is a pressure-sensitive adhesive composition.

According to a certain embodiment of the invention, the hydrophobic outer phase is a pressure-sensitive adhesive composition comprising a polymer or polymer mixture which is Ware pressure-sensitive adhesives polymer(s) selected from the group of polysiloxanes, polyisobutylenes, polyacrylates, copolymers of styrene and butadiene, copolymers of styrene and isoprene, preferably selected from the group of polysiloxanes, or polyisobutylenes.

Pressure-sensitive adhesive polymers being suitable for a hot-melt coating exhibit a dynamic viscosity of no more than 60 Pa·s, no more than 80 Pa·s, no more than 100 Pa·s, no more than 120 Pa·s or at most 150 Pa·s at a temperature of 160° C. Depending on the dynamic viscosity of the pressure-sensitive adhesive polymer(s) at 160° C., the addition of a softener, such as waxes, silicone oils, glycerin, condensates from glycerin with fatty acids or polyols, or laurylacetate, or, in particular, glycerolmonolaurate, laurylacetate, waxes of the formula R—C(O)—OR', alkylmethylsiloxane waxes, siloxated polyether waxes, organic waxes or glycerin, may be required to adjust the viscosity of the pressure-sensitive adhesive polymer(s) in a suitable manner during hot-melt manufacturing processes.

Pressure-sensitive adhesive polymers being suitable for solvent-containing coating mixtures exhibit a dynamic viscosity of above 150 Pa·s at a temperature of 160° C. and therefore require the addition of a softener in order to be suitable for a hot-melt manufacturing process.

According to a certain embodiment of the invention, the pressure-sensitive adhesive composition does not contain a softener, which after the addition to a pressure-sensitive adhesive composition lowers the viscosity of said pressure-sensitive adhesive composition to no more than 60 Pa·s, no more than 80 Pa·s, no more than 100 Pa·s, no more than 120 Pa·s or at most 150 Pa·s at a temperature of 160° C.

According to a certain embodiment of the invention, the outer phase does not contain a pressure-sensitive adhesive composition having a dynamic viscosity of no more than 60 Pa·s, no more than 80 Pa·s, no more than 100 Pa·s, no more than 120 P·s or at most 150 Pa·s at a temperature of 160° C.

In certain embodiments of the invention, the polymer or polymer mixture in the outer phase is a/are pressure-sensitive adhesive polymer(s) selected from the group of polysiloxanes, polyisobutylenes, polyacrylates, copolymers of styrene and butadiene, copolymers of styrene and isoprene, preferably selected from the group of polysiloxanes, or polyisobutylenes.

In a certain preferred embodiment of the invention, the polymer or polymer mixture in the outer phase is a/are pressure-sensitive adhesive polysiloxane(s). Pressure-sensitive adhesive polysiloxanes provide for suitable tack for quick bonding to various skin types, including wet skin, suitable adhesive and cohesive qualities, long lasting adhesion to the skin of up to 7 days, a high degree of flexibility, a permeability to moisture, and compatibility to many actives and film-substrates. It is possible to provide them with sufficient amine resistance and therefore enhanced stability in the presence of amines. Such pressure-sensitive adhesive polymers are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The dimethiconol content contributes to the viscous component of the visco-elastic behavior, and impacts the wetting and the spreadability properties of the adhesive. The resin acts as a tackifying and reinforcing agent, and participates in the elastic component. The correct balance between dimethiconol and resin provides for the correct adhesive properties.

The adhesive strength of the pressure-sensitive polysiloxanes may be sufficient for the desired skin contact. In certain embodiments of the invention a plasticizer or a tackifying agent is incorporated into the formulation to improve the adhesive characteristics of the biphasic layer. It may be advantageous in an individual case to improve the tack by adding small amounts of tackifiers.

Preferred pressure-sensitive adhesive polymers are supplied and used in solvents like heptane, ethyl acetate or other volatile silicone fluids. For the present invention pressure-sensitive adhesive mixtures of pressure-sensitive adhesive polysiloxane(s) in heptane or ethyl acetate are preferred. The solids content is usually between 60 and 80%.

The preferred pressure-sensitive adhesive mixtures of pressure-sensitive adhesive polysiloxane(s) in heptane in accordance with the invention are characterized by a solution viscosity at 25° C. and 60% solids content in heptane of more than 150 mPa·s, or from about 200 mPa·s to about 700 mPa·s, in particular from about 350 mPa·s to about 600 mPa·s, more preferred from about 480 mPa·s to about 550 mPa·s, or most preferred of about 500 mPa·s or alternatively from about 400 mPa·s to about 480 mPa·s, or most preferred of about 450 mPa·s. These may also be characterized by a complex viscosity at 0.01 rad/s at 30° C. of less than about $1\times10^9$ Poise or from about $1\times10^5$ to about $9\times10^8$ Poise, or more preferred from about $1\times10^5$ to about $1\times10^7$ Poise, or most preferred about $5\times10^6$ Poise or alternatively more preferred from about $2\times10^7$ to about $9\times10^8$ Poise, or most preferred about $1\times10^8$ Poise.

The preferred pressure-sensitive adhesive mixtures of pressure-sensitive adhesive polysiloxane(s) in ethyl acetate in accordance with the invention are characterized by a solution viscosity at 25° C. and 60% solids content in ethyl acetate of more than 350 mPa·s, or from about 400 mPa·s to about 1500 mPa·s, in particular from about 600 mPa·s to about 1300 mPa·s, more preferred from about 1100 mPa·s to about 1300 mPa·s, or most preferred of about 1200 mPa·s or alternatively from about 700 mPa·s to about 900 mPa·s, or most preferred of about 800 mPa·s. These may also be characterized by a complex viscosity at 0.01 rad/s at 30° C. of less than about $1\times10^9$ Poise or from about $1\times10^5$ to about $9\times10^8$ Poise, or more preferred from about $1\times10^5$ to about $1\times10^7$ Poise, or most preferred about $5\times10^6$ Poise or alternatively more preferred from about $2\times10^7$ to about $9\times10^8$ Poise, or most preferred about $1\times10^8$ Poise.

According to a certain embodiment, a pressure-sensitive adhesive mixture of a pressure-sensitive adhesive polysiloxane in heptane characterized by a solution viscosity at 25° C. and about 60% solids content in heptane of 500 mPa·s and a pressure-sensitive adhesive polysiloxane in heptane characterized by a solution viscosity at 25° C. and about 60% solids content in heptane of 450 mPa·s is preferred.

According to a certain other embodiment, a pressure-sensitive adhesive mixture of a pressure-sensitive adhesive polysiloxane in ethyl acetate characterized by a solution viscosity at 25° C. and about 60% solids content in ethyl acetate of 1200 mPa·s and a pressure-sensitive adhesive polysiloxane in ethyl acetate characterized by a solution viscosity at 25° C. and about 60% solids content in ethyl acetate of 800 mPa·s is preferred.

Suitable pressure-sensitive adhesive polysiloxanes may be obtained from DOW CORNING® BIO-PSA Standard Silicone Adhesives. Preferred pressure-sensitive adhesive mixtures of pressure-sensitive adhesive polysiloxane(s) in heptane are the BIO-PSA 7-4301 and BIO-PSA 7-4201 Silicone Adhesives, and in ethyl acetate the BIO-PSA 7-4302 and BIO-PSA 7-4202 Silicone Adhesives. According to certain embodiments of the invention, a mixture of BIO-PSA 7-4301 and BIO-PSA 7-4201 is preferred and according to certain other embodiments a mixture of BIO-PSA 7-4302 and BIO-PSA 7-4202 is preferred. According to certain embodiments the preferred mixtures provide a 50:50 ratio, according to certain other embodiments the mixtures provide a 60:40, or 70:30 ratio.

BIO-PSA 7-4301 has a solution viscosity at 25° C. and about 60% solids content in heptane of 500 mPa·s and a complex viscosity at 0.01 rad/s at 30° C. of $5 \times 10^6$ Poise. BIO-PSA 7-4201 has a solution viscosity at 25° C. and 60% solids content in heptane of 450 mPa·s and a complex viscosity at 0.01 rad/s at 30° C. of $1 \times 10^8$ Poise. BIO-PSA 7-4302 has a solution viscosity at 25° C. and about 60% solids content in ethyl acetate of 1200 mPa·s and a complex viscosity at 0.01 rad/s at 30° C. of $5 \times 10^6$ Poise. BIO-PSA 7-4202 has a solution viscosity at 25° C. and about 60% solids content in heptane of 800 mPa·s and a complex viscosity at 0.01 rad/s at 30° C. of $1 \times 10^8$ Poise.

According to certain embodiments of the invention, therapeutically effective amounts of the active agent are provided for 1 to 7 days by the transdermal therapeutic system during an administration period to the skin of the patient of 1 to 7 days.

According to certain embodiments of the invention, therapeutically effective amounts of the active agent are provided for 1 day by the transdermal therapeutic system according to the invention during an administration period to the skin of the patient of 1 day.

According to certain embodiments of the invention, therapeutically effective amounts of the active agent are provided for 3 days by the transdermal therapeutic system according to the invention during an administration period to the skin of the patient of 3 days, preferably for 4 days during an administration period to the skin of the patient of 4 days, or for 7 days during an administration period to the skin of the patient of 7 days.

EXAMPLES

The present invention will now be more fully described with reference to the accompanying examples. It should be understood, however, that the following description is illustrative only and should not be taken in any way as a restriction of the invention.

Example 1

The composition of the active agent-containing biphasic coating mixtures is summarized in Table 1 below.

TABLE 1

| Excipients | Solid [%] | Solution [%] |
|---|---|---|
| Rotigotine | 7.50 | 4.665 |
| Polyvinylpyrrolidone (Kollidon 90 F) | 3.33 | 2.07 |
| Ethanol | — | 14.04 |
| Sodium metabisulfite solution (10% w/w) | 0.0015 | 0.0093 |
| Ascorbyl palmitate | 0.017 | 0.010 |
| DL-α-Tocopherol | 0.042 | 0.026 |
| BIO-PSA Q7-4301 (70.0% w/w) | 53.47 | 47.515 |
| BIO-PSA Q7-4201 (70.0% w/w) | 35.64 | 31.67 |
| Total | 100.00 | 100.005 |

Preparation of the Rotigotine-Containing Biphasic Coating Mixture (Step 1):

6.66 g polyvinylpyrrolidone (PVP, KOLLIDON® 90 F), 0.083 g DL-α-Tocopherol, 0.033 g ascorbyl palmitate and 0.030 g of an aqueous sodium metabisulfite solution (10% by weight) were mixed with 25.93 g anhydrous ethanol to obtain a clear solution (300-2000 rpm, propeller stirrer). 15.00 g rotigotine of polymorphic Form II were added while stirring at 300 rpm and heated to 60° C. for 90 min. This mixture was added to 152.80 g silicone adhesive BIO-PSA 7-4301 (70.0% by weight in n-heptane) and 101.84 g silicone adhesive BIO-PSA 7-4201 (70.0% by weight in n-heptane) were added and stirred at 2000 rpm for 10 min (turbine stirrer) to obtain a stable dispersion.

Preparation of the Transdermal Therapeutic System (TTS) (Step 2):

The mixture obtained in step 1 was coated onto a suitable polyester release liner (e.g. SCOTCHPAK™ 9744). The coated release liner sheets were placed in a drying oven and dried at 50° C. for about 30 min and then at 110° C. for about 10 min. The coating thickness was chosen such that removal of the solvents results in an area weight of the rotigotine-containing layer of 60 g/m². The rotigotine-containing layer was laminated with a polyester-type backing foil.

Finally, individual systems (TTS) having a size of 10 cm² were punched out of the rotigotine-containing self-adhesive layer structure and sealed into pouches.

Example 2

The composition of the active agent-containing biphasic coating mixtures is summarized in Table 2 below.

TABLE 2

| Excipients | Solid [%] | Solution [%] |
|---|---|---|
| Rotigotine | 9.00 | 5.48 |
| Polyvinylpyrrolidone (Kollidon 90 F) | 4.00 | 2.43 |
| Ethanol | — | 16.48 |
| Sodium metabisulfite solution (10% w/w) | 0.0018 | 0.011 |
| Ascorbyl palmitate | 0.020 | 0.012 |
| DL-α-Tocopherol | 0.050 | 0.031 |
| BIO-PSA Q7-4301 (70.0% w/w) | 43.46 | 37.78 |
| BIO-PSA Q7-4201 (70.0% w/w) | 43.46 | 37.78 |
| Total | 100.00 | 100.00 |

Preparation of the rotigotine-containing biphasic coating mixture (step 1):

7.01 g polyvinylpyrrolidone (PVP, KOLLIDON® 90F), 0.089 g DL-α-Tocopherol, 0.035 g ascorbyl palmitate and 0.031 g of an aqueous sodium metabisulfite solution (10% by weight) were mixed with 47.45 g anhydrous ethanol to obtain a clear solution (300-2000 rpm, propeller stirrer). 15.76 g rotigotine of polymorphic Form II were added while stirring at 300 rpm and heated to 60° C. for 90 min. This mixture was added to 108.75 g silicone adhesive BIO-PSA 7-4301 (70.0% by weight in n-heptane) and 108.75 g silicone adhesive BIO-PSA 7-4201 (70.0% by weight in n-heptane) were added and stirred at 2000 rpm for 10 min (turbine stirrer) to obtain a stable dispersion.

Preparation of the Transdennal Therapeutic System (TTS) (Step 2):

The mixture obtained in step 1 was coated onto a suitable polyester release liner (e.g. SCOTCHPAK™ 9744). The coated release liner sheets were placed in a drying oven and dried at 50° C. for about 30 min and then at 110° C. for about 10 min. The coating thickness was chosen such that removal of the solvents results in an area weight of the rotigotine-containing layer of 50 g/m². The rotigotine-containing layer was laminated with a polyester-type backing foil.

Finally, individual systems (TTS) having a size of 10 cm² were punched out of the rotigotine-containing self-adhesive layer structure and sealed into pouches.

Example 3

The composition of the active agent-containing biphasic coating mixtures is summarized in Table 3 below.

TABLE 3

| Excipients | Solid [%] | Solution [%] |
|---|---|---|
| Ethanol | — | 10.750 |
| Polyvinylpyrrolidone (Kollidon 90 F) | 8.000 | 4.560 |
| Sodium metabisulfite solution 10% (w/w) | 0.0036 | 0.020 |
| Ascorbyl palmitate | 0.0401 | 0.0228 |
| all-rac-Tocopherol | 0.0994 | 0.0566 |
| Rotigotine | 18.00 | 10.260 |
| BIO PSA 7-4302 (60%) | 36.93 | 35.080 |
| BIO PSA 7-4202 (60%) | 36.93 | 35.080 |
| Ethyl acetate | — | 4.175 |
| Total | 100.00 | 100.00 |
| Solids content | | 57.0% |

Preparation of the Rotigotine-Containing Biphasic Coating Mixture (Step 1):

To a solution of 13.68 g polyvinylpyrrolidone (PVP, KOLLIDON® 90F) in 32.23 g ethanol and 12.52 g ethyl acetate, 0.171 g DL-α-tocopherol, 0.068 g ascorbyl palmitate and 0.062 g of an aqueous sodium metabisulfite solution (10% by weight) were added and mixed to obtain a clear solution (1000 rpm, propeller stirrer). 105.24 g silicone adhesive BIO-PSA 7-4202 (60% by weight in ethyl acetate) and 105.24 g silicone adhesive BIO-PSA 7-4302 (60% by weight in ethyl acetate) were added to the obtained PVP solution and stirred at 500 rpm until complete mixing. 30.78 g rotigotine of polymorphic Form Il were added while stirring. The mixture was heated up to 40° C. and stirred at 500 rpm for a minimum of 60 min until a homogenous dispersion was obtained.

Preparation of the Transdermal Therapeutic System (TTS) (Step 2):

The mixture obtained in step 1 was coated onto two sheets of a suitable polyester release liner (e.g. SCOTCHPAK™ 9755). The coated release liner sheets were placed in a drying oven and dried at 50° C. for about 30 min and then at 115° C. for about 10 min. The coating thickness was chosen such that removal of the solvents results in a coating weight of each of the two rotigotine-containing layers of 75 g/m². The first rotigotine-containing layer was laminated with (1) a polyester-type backing foil and (2) the second rotigotine-containing layer after removal of the release liner from the surface of the first layer to provide the rotigotine-containing self-adhesive layer structure with a rotigotine-containing biphasic layer having an area weight of 150 g/m².

Finally, individual systems (TTS) having a size of 10 cm² were punched out of the rotigotine-containing self-adhesive layer structure and sealed into pouches.

Example 4

In Example 4, the in-vitro permeation of Examples 1 to 3 was evaluated by a membrane permeation test using a 51 µm thick membrane consisting of an ethylene vinyl acetate (EVA) copolymer with 9% vinyl acetate (COTRAN™ Membrane, 3M) and the Paddle over Disk apparatus described in the United States Pharmacopeia (USP). Phosphate buffer pH 4.5 was used as acceptor medium (900 ml; 32° C.; 50 rpm). TTS with an area of 10 cm² of Example 1, 2 and 3 were tested. The permeation of rotigotine into the acceptor medium was measured by HPLC. The results are shown in Tables 4 and 5 and FIG. 1.

TABLE 4

| | rotigotine permeation [µg/cm²] n = 3 (SD) | | |
|---|---|---|---|
| Time [h] | Example 1 | Example 2 | Example 3 |
| 0 | 0.00 (0.00) | 0.00 (0.00) | 0.00 (0.00) |
| 4 | 23.26 (0.92) | 28.00 (1.55) | 37.27 (4.40) |
| 8 | 63.42 (1.84) | 74.67 (2.16) | 82.49 (7.09) |
| 12 | 115.33 (2.16) | 125.67 (2.80) | 128.82 (4.17) |
| 16 | 166.67 (2.64) | 179.33 (2.42) | 183.90 (2.07) |
| 20 | 220.03 (2.99) | 232.67 (1.63) | 235.10 (2.48) |
| 24 | 272.01 (4.10) | 284.83 (0.75) | 287.11 (2.31) |
| 28 | 324.33 (4.42) | 336.50 (1.05) | 339.69 (2.26) |
| 32 | 376.14 (5.34) | 386.83 (1.83) | 392.64 (1.98) |
| 36 | 411.96 (2.53) | 431.50 (3.39) | 445.75 (1.95) |
| 40 | 427.08 (2.17) | 457.67 (7.06) | 498.61 (1.63) |
| 44 | 433.77 (1.47) | 468.67 (9.79) | 551.23 (1.58) |
| 48 | — | — | 602.71 (1.72) |
| 52 | — | — | 656.10 (1.77) |
| 56 | — | — | 709.57 (2.04) |
| 60 | — | — | 762.62 (2.69) |
| 64 | — | — | 815.21 (3.78) |
| 68 | — | — | 867.34 (4.32) |
| 72 | — | — | 919.19 (5.34) |
| 76 | — | — | 969.86 (5.59) |
| 80 | — | — | 1021.38 (6.16) |
| 84 | — | — | 1073.09 (6.43) |
| 88 | — | — | 1123.22 (7.52) |
| 92 | — | — | 1172.30 (8.19) |
| 96 | — | — | 1221.74 (9.81) |
| 100 | — | — | 1271.46 (10.86) |
| 104 | — | — | 1320.81 (11.32) |
| 108 | — | — | 1369.46 (12.72) |
| 112 | — | — | 1415.27 (13.63) |
| 116 | — | — | 1460.86 (13.10) |
| 120 | — | — | 1507.33 (14.18) |
| 124 | — | — | 1553.71 (15.26) |
| 128 | — | — | 1600.48 (16.81) |
| 132 | — | — | 1646.49 (17.41) |
| 136 | — | — | 1691.47 (19.29) |
| 140 | — | — | 1736.65 (20.78) |
| 144 | — | — | 1780.74 (21.97) |
| 148 | — | — | 1825.03 (22.41) |
| 152 | — | — | 1869.91 (24.75) |
| 156 | — | — | 1914.56 (25.78) |

TABLE 4-continued rotigotine permeation [µg/cm$^2$] n = 3 (SD)

| Time [h] | Example 1 | Example 2 | Example 3 |
|---|---|---|---|
| 160 | — | — | 1958.29 (26.57) |
| 164 | — | — | 2000.87 (27.32) |
| 168 | — | — | 2045.11 (28.02) |
| 172 | — | — | 2087.75 (29.56) |
| 176 | — | — | 2130.92 (30.79) |
| 180 | — | — | 2174.24 (32.05) |
| 184 | — | — | 2216.06 (35.01) |
| 188 | — | — | 2257.11 (35.84) |
| 192 | — | — | 2299.36 (37.55) |

TABLE 5 rotigotine permeation [µg/cm$^2$/h] n = 3 (SD)

| Time [h] | Example 1 | Example 2 | Example 3 |
|---|---|---|---|
| 0 | 0.00 (0.00) | 0.00 (0.00) | 0.00 (0.00) |
| 4 | 5.82 (0.23) | 7.00 (0.39) | 9.32 (1.10) |
| 8 | 10.04 (0.31) | 11.67 (0.26) | 11.30 (0.77) |
| 12 | 12.98 (0.39) | 12.75 (0.27) | 11.58 (1.12) |
| 16 | 12.83 (0.32) | 13.42 (0.20) | 13.77 (1.11) |
| 20 | 13.34 (0.34) | 13.33 (0.26) | 12.80 (0.11) |
| 24 | 13.00 (0.47) | 13.04 (0.29) | 13.00 (0.18) |
| 28 | 13.08 (0.38) | 12.92 (0.26) | 13.14 (0.16) |
| 32 | 12.95 (0.65) | 12.58 (0.34) | 13.24 (0.13) |
| 36 | 8.96 (0.80) | 11.17 (0.44) | 13.28 (0.02) |
| 40 | 3.78 (0.44) | 6.54 (1.03) | 13.21 (0.19) |
| 44 | 1.67 (0.48) | 2.75 (0.69) | 13.15 (0.10) |
| 48 | — | — | 12.87 (0.06) |
| 52 | — | — | 13.35 (0.09) |
| 56 | — | — | 13.37 (0.36) |
| 60 | — | — | 13.26 (0.26) |
| 64 | — | — | 13.15 (0.28) |
| 68 | — | — | 13.03 (0.18) |
| 72 | — | — | 12.96 (0.26) |
| 76 | — | — | 12.67 (0.10) |
| 80 | — | — | 12.88 (0.16) |
| 84 | — | — | 12.93 (0.09) |
| 88 | — | — | 12.53 (0.28) |
| 92 | — | — | 12.27 (0.17) |
| 96 | — | — | 12.36 (0.41) |
| 100 | — | — | 12.43 (0.34) |
| 104 | — | — | 12.34 (0.12) |
| 108 | — | — | 12.16 (0.36) |
| 112 | — | — | 11.45 (0.25) |
| 116 | — | — | 11.40 (0.13) |
| 120 | — | — | 11.62 (0.28) |
| 124 | — | — | 11.60 (0.27) |
| 128 | — | — | 11.69 (0.40) |
| 132 | — | — | 11.50 (0.18) |
| 136 | — | — | 11.25 (0.47) |
| 140 | — | — | 11.30 (0.37) |
| 144 | — | — | 11.02 (0.30) |
| 148 | — | — | 11.07 (0.27) |
| 152 | — | — | 11.22 (0.61) |
| 156 | — | — | 11.16 (0.26) |
| 160 | — | — | 10.93 (0.20) |
| 164 | — | — | 10.64 (0.28) |
| 168 | — | — | 11.06 (0.31) |
| 172 | — | — | 10.66 (0.44) |
| 176 | — | — | 10.79 (0.40) |
| 180 | — | — | 10.83 (0.41) |
| 184 | — | — | 10.45 (0.74) |
| 188 | — | — | 10.26 (0.24) |
| 192 | — | — | 10.56 (0.43) |

Example 5

The composition of the rotigotine-containing biphasic coating mixture is summarized in Table 6 below.

TABLE 6

| Excipients | Solid [%] | Solution [%] |
|---|---|---|
| Ethanol | — | 12.28 |
| Ethyl acetate | — | 3.39 |
| Polyvinylpyrrolidone (Kollidon 90 F) | 4.00 | 2.28 |
| Polyvinylpyrrolidone (Kollidon 30) | 6.00 | 3.42 |
| Sodium metabisulfite solution 10% (w/w) | 0.0045 | 0.03 |
| Ascorbyl palmitate | 0.04 | 0.02 |
| all-rac-Tocopherol | 0.10 | 0.06 |
| Rotigotine | 18.00 | 10.26 |
| BIO PSA 7-4302 (60%) | 35.93 | 34.13 |
| BIO PSA 7-4202 (60%) | 35.93 | 34.13 |
| Total | 100.00 | 100.00 |
| Solids content | | 57.0% |

Preparation of the Rotigotine-Containing Biphasic Coating Mixture (Step 1):

13.68 g polyvinylpyrrolidone (PVP, KOLLIDON® 90F) and 20.53 g polyvinylpyrrolidone (PVP, KOLLIDON® 30) were dissolved in 73.67 g ethanol and 20.53 g ethyl acetate. 0.34 g DL-α-tocopherol, 0.14 g ascorbyl palmitate and 0.15 g of an aqueous sodium metabisulfite solution (10% by weight) were added and mixed to obtain a clear solution (1000 rpm, propeller stirrer). 204.81 g silicone adhesive BIO-PSA 7-4202 (60% by weight in ethyl acetate) and 204.81 g silicone adhesive BIO-PSA 7-4302 (60% by weight in ethyl acetate) were added to the obtained PVP solution and stirred at 500 rpm until complete mixing. 61.56 g rotigotine of polymorphic Form II were added while stirring. The mixture was heated up to 40° C. and stirred at 500 rpm for a minimum of 60 min until a homogenous dispersion was obtained.

Preparation of the transdermal therapeutic system (TTS) (step 2):

The mixture obtained in step 1 was coated onto two sheets of a suitable polyester release liner (e.g. SCOTCHPAK™ 9755). The coated release liner sheets were placed in a drying oven and dried at 50° C. for about 30 min and then at 115° C. for about 10 min. The coating thickness was chosen such that removal of the solvents results in a coating weight of each of the two rotigotine-containing layers of 80-82 g/m$^2$. The first rotigotine-containing layer was laminated with (1) a polyester-type backing foil and (2) the second rotigotine-containing layer after removal of the release liner from the surface of the first layer to provide the rotigotine-containing self-adhesive layer structure with a rotigotine-containing biphasic layer having a coating weight of 160-164 g/m$^2$. Finally, individual systems (TTS) having a size of 10 cm$^2$ were punched out of the rotigotine-containing self-adhesive layer structure and sealed into pouches.

Example 6

The composition of the rotigotine-containing biphasic coating reservoir mixture is identical to Example 5.

The composition of the rotigotine-free skin contact layer is summarized in Table 7 below.

TABLE 7

| Excipients | Solid [%] | Solution [%] |
|---|---|---|
| BIO PSA 7-4302 (60%) | 80.00 | 80.00 |
| BIO PSA 7-4202 (60%) | 20.00 | 20.00 |
| Total | 100.00 | 100.00 |

Preparation of the Rotigotine-Free Adhesive Mixture (Step 1):

80.01 g silicone adhesive BIO-PSA 7-4202 (60% by weight in ethyl acetate) were added to 320.01 g silicone adhesive BIO-PSA 7-4302 (60% by weight in ethyl acetate) and stirred at 500 rpm until complete mixing.

Preparation of the Rotigotine-Free Skin Layer (TTS) (Step 2):

The adhesive mixture obtained in step 1 was coated onto sheets of a suitable polyester release liner (e.g. SCOTCH-PAK' 9755). The coated release liner sheets were placed in a drying oven and dried at 50° C. for about 30 min and then at 115° C. for about 10 min. The coating thickness was chosen such that removal of the solvents results in a coating weight of each of the adhesive layer of 28 g/m$^2$.

Preparation of the rotigotine-containing biphasic coating mixture (step 3) is identical to step 1 in Example 5.

Preparation of the Transdermal Therapeutic System (TTS) (Step 4):

The mixture obtained in step 3 was coated onto sheets of a suitable polyester release liner (e.g. SCOTCHPAK™ 9755). The coated release liner sheets were placed in a drying oven and dried at 50° C. for about 30 min and then at 115° C. for about 10 min. The coating thickness was chosen such that removal of the solvents results in a coating weight of the rotigotine-containing layer of 139 g/m$^2$. The rotigotine-containing layer was laminated with (1) a polyester-type backing foil and (2) the rotigotine-free skin layer of step 2 to provide the rotigotine-containing self-adhesive layer structure with a rotigotine-containing biphasic layer having a coating weight of 167 g/m$^2$. Finally, individual systems (TTS) having a size of 10 cm$^2$ were punched out of the rotigotine-containing self-adhesive layer structure and sealed into pouches.

Example 7

The composition of the rotigotine-containing biphasic coating mixture as rotigotine-containing skin contact layer is summarized in Table 8 below.

TABLE 8

| Excipients | Solid [%] | Solution [%] |
|---|---|---|
| Ethanol | — | 7.84 |
| Polyvinylpyrrolidone (Kollidon 90 F) | 3.33 | 1.93 |
| Sodium metabisulfite solution 10% (w/w) | 0.015 | 0.01 |
| Ascorbyl palmitate | 0.02 | 0.01 |
| all-rac-Tocopherol | 0.04 | 0.02 |
| Rotigotine | 7.50 | 4.34 |
| BIO PSA 7-4302 (60%) | 71.29 | 68.68 |
| BIO PSA 7-4202 (60%) | 17.82 | 17.17 |
| Total | 100.00 | 100.00 |
| Solids content | | 57 |

Preparation of the Rotigotine-Containing Biphasic Coating Mixture (Step 1):

3.34 g polyvinylpyrrolidone (PVP, KOLLIDON® 90F) were dissolved in 13.56 g ethanol. 0.02 g DL-α-tocopherol, 0.04 g ascorbyl palmitate and 0.15 g of an aqueous sodium metabisulfite solution (10% by weight) were added and mixed to obtain a clear solution (1000 rpm, propeller stirrer). 29.70 g silicone adhesive BIO-PSA 7-4202 (60% by weight in ethyl acetate) and 118.80 g silicone adhesive BIO-PSA 7-4302 (60% by weight in ethyl acetate) were added to the obtained PVP solution and stirred at 500 rpm until complete mixing. 7.51 g rotigotine of polymorphic Form II were added while stirring. The mixture was heated up to 40° C. and stirred at 500 rpm for a minimum of 60 min until a homogenous dispersion was obtained.

Preparation of the Transdermal Therapeutic System (TTS) (Step 2):

The mixture obtained in step 1 was coated onto sheets of a suitable polyester release liner (e.g. SCOTCHPAK™ 9755). The coated release liner sheets were placed in a drying oven and dried at 50° C. for about 30 min and then at 115° C. for about 10 min. The coating thickness was chosen such that removal of the solvents results in a coating weight of each of the rotigotine-containing layer of 28 g/m$^2$. The rotigotine-containing layer was laminated with (1) a polyester-type backing foil and (2) the rotigotine-containing layer of Example 6 with a coating weight of 188-192 g/m$^2$ after removal of the release liner from the surface of the first layer to provide the rotigotine-containing self-adhesive layer structure with a rotigotine-containing biphasic layer having a total coating weight of 160-164 g/m$^2$. Finally, individual systems (TTS) having a size of 10 cm$^2$ were punched out of the rotigotine-containing self-adhesive layer structure and sealed into pouches.

Example 8

Figure 2:
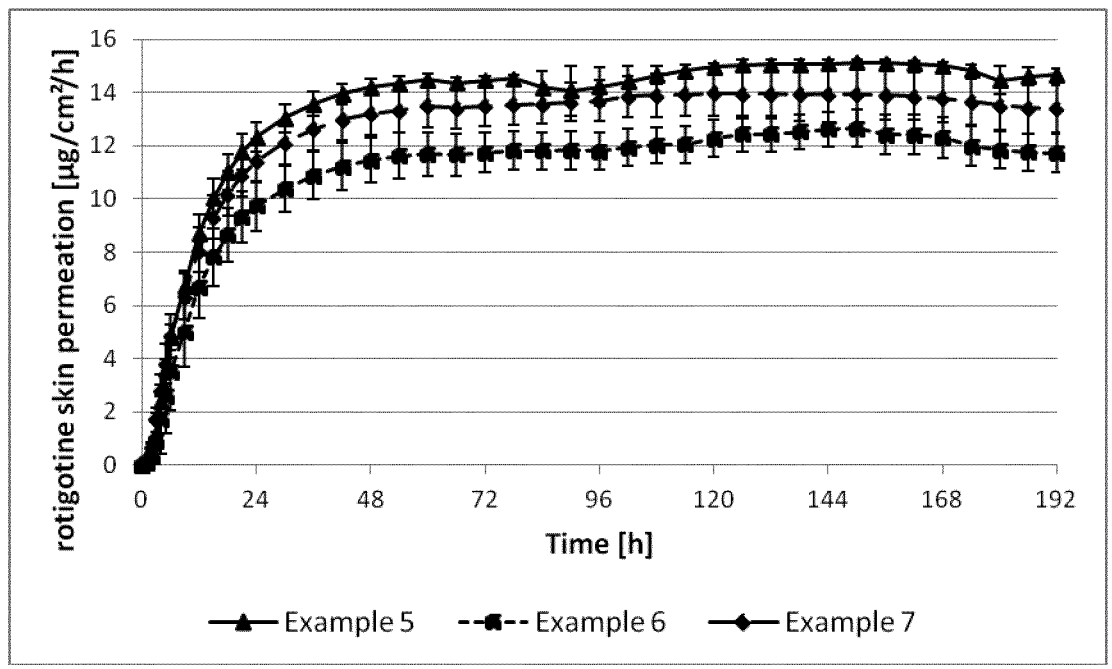
FIG. 2 depicts the skin permeation rate of Example 5, Example 6 and Example 7.

In Example 8, the in-vitro skin permeation of Examples 5, 6 and 7 was evaluated by in-vitro skin permeation test performed over 192 hours using dermatomized human skin of about 300 μm thickness in a flow cell setup. A phosphate buffered saline (PBS) pH 6.2 was used as acceptor medium (32° C.) and the area of the acceptor cells was 0.52 cm$^2$. Samples were taken every hour for the first 6 hours, every 3 hours until 18 hours and every 6 hours for the remaining time of the experiments. The permeation of rotigotine into the acceptor medium was determined by HPLC. The results are shown in Tables 9 and 10 and FIG. 2.

TABLE 9

| | rotigotine skin permeation [μg/cm$^2$] n = 3 (SD) | | |
|---|---|---|---|
| Time [h] | Example 5 | Example 6 | Example 7 |
| 0 | 0.00 (0.00) | 0.00 (0.00) | 0.00 (0.00) |
| 1 | 0.08 (0.06) | 0.11 (0.02) | 0.12 (0.01) |
| 2 | 0.40 (0.07) | 0.43 (0.15) | 0.77 (0.56) |
| 3 | 1.57 (0.16) | 1.35 (0.60) | 2.48 (1.61) |
| 4 | 3.95 (0.38) | 3.08 (1.24) | 5.24 (2.89) |
| 5 | 7.57 (0.73) | 5.69 (1.98) | 9.04 (4.28) |
| 6 | 12.36 (1.20) | 9.18 (2.79) | 13.91 (5.69) |
| 9 | 32.46 (3.07) | 24.19 (5.30) | 32.94 (9.63) |
| 12 | 58.53 (5.22) | 44.27 (7.71) | 57.17 (13.11) |
| 15 | 88.64 (7.35) | 67.75 (10.09) | 85.12 (16.34) |
| 18 | 121.66 (9.38) | 93.70 (12.50) | 115.73 (19.40) |
| 21 | 156.98 (11.35) | 121.63 (14.84) | 148.41 (22.29) |
| 24 | 193.94 (13.04) | 150.86 (17.22) | 182.68 (25.08) |
| 30 | 272.15 (16.19) | 213.11 (22.01) | 255.45 (30.34) |
| 36 | 353.62 (18.88) | 278.34 (26.84) | 331.15 (35.72) |
| 42 | 437.33 (21.09) | 345.64 (31.65) | 409.14 (40.97) |
| 48 | 522.53 (22.85) | 414.33 (36.44) | 488.38 (46.06) |

TABLE 9-continued rotigotine skin permeation [µg/cm²] n = 3 (SD)

| Time [h] | Example 5 | Example 6 | Example 7 |
|---|---|---|---|
| 54 | 608.55 (24.49) | 484.11 (41.37) | 568.40 (51.16) |
| 60 | 695.40 (25.73) | 554.21 (46.28) | 649.42 (56.18) |
| 66 | 781.61 (26.99) | 624.16 (50.92) | 729.93 (60.86) |
| 72 | 868.28 (28.02) | 694.63 (55.52) | 810.85 (65.41) |
| 78 | 955.51 (28.77) | 765.50 (60.06) | 892.13 (69.80) |
| 84 | 1040.63 (30.06) | 836.39 (64.27) | 973.52 (74.00) |
| 90 | 1124.99 (32.68) | 907.33 (68.39) | 1055.32 (78.31) |
| 96 | 1210.24 (35.12) | 978.08 (72.67) | 1137.45 (82.47) |
| 102 | 1296.73 (37.18) | 1049.66 (76.80) | 1220.56 (86.66) |
| 108 | 1384.60 (38.69) | 1121.75 (81.20) | 1303.98 (90.84) |
| 114 | 1473.52 (39.81) | 1194.00 (85.44) | 1387.47 (95.07) |
| 120 | 1563.25 (40.67) | 1267.62 (90.44) | 1471.27 (99.28) |
| 126 | 1653.44 (41.87) | 1342.30 (95.93) | 1554.91 (103.32) |
| 132 | 1743.80 (42.84) | 1416.98 (101.50) | 1638.61 (107.32) |
| 138 | 1834.18 (43.78) | 1492.10 (107.37) | 1722.20 (111.18) |
| 144 | 1924.70 (44.69) | 1567.82 (113.79) | 1805.90 (115.12) |
| 150 | 2015.42 (45.48) | 1643.71 (120.18) | 1889.45 (119.23) |
| 156 | 2106.00 (46.33) | 1718.18 (125.54) | 1972.81 (123.60) |
| 162 | 2196.52 (47.00) | 1792.63 (130.85) | 2055.97 (128.00) |
| 168 | 2286.50 (47.82) | 1866.46 (136.22) | 2138.73 (132.36) |
| 174 | 2375.57 (48.91) | 1938.38 (140.51) | 2220.66 (136.65) |
| 180 | 2462.37 (51.96) | 2009.42 (144.89) | 2301.77 (140.58) |
| 186 | 2549.97 (54.03) | 2079.95 (149.31) | 2382.35 (144.54) |
| 192 | 2637.99 (55.34) | 2150.31 (153.14) | 2462.66 (148.56) |

TABLE 10 rotigotine skin permeation rate [µg/cm²/h] n = 3 (SD)

| Time [h] | Example 5 | Example 6 | Example 7 |
|---|---|---|---|
| 0 | 0.00 (0.00) | 0.00 (0.00) | 0.00 (0.00) |
| 1 | 0.09 (0.06) | 0.11 (0.02) | 0.14 (0.03) |
| 2 | 0.32 (0.03) | 0.32 (0.17) | 0.66 (0.55) |
| 3 | 1.17 (0.09) | 0.92 (0.46) | 1.70 (1.05) |
| 4 | 2.38 (0.22) | 1.73 (0.63) | 2.76 (1.28) |
| 5 | 3.61 (0.35) | 2.61 (0.74) | 3.80 (1.39) |
| 6 | 4.79 (0.47) | 3.48 (0.81) | 4.86 (1.41) |
| 9 | 6.70 (0.62) | 5.00 (0.85) | 6.34 (1.31) |
| 12 | 8.69 (0.72) | 6.69 (0.84) | 8.08 (1.16) |
| 15 | 10.04 (0.71) | 7.83 (0.83) | 9.32 (1.08) |
| 18 | 11.00 (0.68) | 8.65 (0.84) | 10.20 (1.02) |
| 21 | 11.77 (0.67) | 9.31 (0.81) | 10.89 (0.96) |
| 24 | 12.32 (0.57) | 9.74 (0.81) | 11.42 (0.93) |
| 30 | 13.04 (0.54) | 10.37 (0.81) | 12.13 (0.88) |
| 36 | 13.58 (0.47) | 10.87 (0.81) | 12.62 (0.90) |
| 42 | 13.95 (0.39) | 11.22 (0.81) | 13.00 (0.88) |
| 48 | 14.20 (0.31) | 11.45 (0.80) | 13.21 (0.85) |
| 54 | 14.34 (0.29) | 11.63 (0.82) | 13.34 (0.85) |
| 60 | 14.47 (0.22) | 11.68 (0.82) | 13.50 (0.84) |
| 66 | 14.37 (0.21) | 11.66 (0.78) | 13.42 (0.78) |
| 72 | 14.44 (0.17) | 11.74 (0.78) | 13.49 (0.76) |
| 78 | 14.54 (0.13) | 11.81 (0.78) | 13.55 (0.73) |
| 84 | 14.19 (0.62) | 11.81 (0.73) | 13.56 (0.70) |
| 90 | 14.06 (0.92) | 11.82 (0.73) | 13.63 (0.72) |
| 96 | 14.21 (0.73) | 11.79 (0.78) | 13.69 (0.69) |
| 102 | 14.42 (0.57) | 11.93 (0.77) | 13.85 (0.70) |
| 108 | 14.64 (0.33) | 12.02 (0.82) | 13.90 (0.70) |
| 114 | 14.82 (0.20) | 12.04 (0.80) | 13.92 (0.71) |
| 120 | 14.95 (0.15) | 12.27 (0.84) | 13.97 (0.70) |
| 126 | 15.03 (0.20) | 12.45 (0.92) | 13.94 (0.68) |
| 132 | 15.06 (0.16) | 12.45 (0.94) | 13.95 (0.67) |
| 138 | 15.06 (0.16) | 12.52 (1.00) | 13.93 (0.65) |
| 144 | 15.09 (0.15) | 12.62 (1.09) | 13.95 (0.67) |
| 150 | 15.12 (0.14) | 12.65 (1.08) | 13.92 (0.70) |
| 156 | 15.10 (0.15) | 12.41 (0.90) | 13.89 (0.74) |
| 162 | 15.09 (0.12) | 12.41 (0.89) | 13.86 (0.75) |
| 168 | 15.00 (0.14) | 12.31 (0.90) | 13.79 (0.75) |
| 174 | 14.85 (0.18) | 11.99 (0.88) | 13.66 (0.75) |
| 180 | 14.47 (0.54) | 11.84 (0.95) | 13.52 (0.70) |
| 186 | 14.60 (0.35) | 11.75 (0.98) | 13.43 (0.71) |
| 192 | 14.67 (0.22) | 11.73 (0.91) | 13.39 (0.73) |

The invention claimed is:

1. A method of preparing transdermal therapeutic systems having constant permeation rates during an administration period comprising forming a transdermal therapeutic system with an active-agent-containing layer in the form of a dried biphasic layer, which is not a hot-melt layer, having a hydrophilic inner phase and a hydrophobic outer phase, wherein:
   the inner phase comprises an additive and an active agent consisting of dissolved active agent therein; and the additive consists of additive having a higher affinity to water than to the active agent; and
   said method comprising (a) selecting an amount of the active agent in the inner phase of the biphasic layer to correspond to a predetermined desired administration period of 1 to 7 days in order to administer the active agent for the predetermined desired administration period, and
   (b) dissolving the selected amount of the active agent and an amount of additive in the inner phase to maintain a constant permeation rate within 20% points during the predetermined desired administration period in step (a), and
   (c) coating the biphasic layer at a coating weight ranging from 100 to 400 g/m²,
   with the dissolved active agent present within the biphasic layer in a concentration of about 7.5 to 25 weight %,
   wherein said selecting step comprises reducing the amount of the active agent required for diffusion based on cutaneous water displacement,
   said active agent is rotigotine, said hydrophobic outer layer comprises pressure-sensitive adhesive(s) in ethyl acetate,
   said dissolving step comprises a heating step consisting of heating at 40° C.,
   and wherein said additive is a mixture of polyvinylpyrrolidone having a K-Value of from 80 to 200 and polyvinylpyrrolidone having a K-value of 10 to 79, resulting in a higher permeation rate at 192 hours versus 24 hours.

2. The method in accordance with claim 1, wherein said hydrophobic outer phase is pressure-sensitive adhesive polysiloxane and method further comprises incorporating from 18 to 25% rotigotine.

3. The method in accordance with claim 1, wherein said hydrophobic outer phase is formed from pressure-sensitive-adhesive consisting of polysiloxane(s), the predetermined desired administration period is from 3 to 7 days and said method further comprises applying a skin-adhesive layer formed from pressure-sensitive adhesive consisting of polysiloxane(s).

4. The method in accordance with claim 3, further comprising incorporating active ingredient rotigotine-adhesive layer.

5. The method in accordance with claim 1, wherein the biphasic layer is applied at a coating weight ranging from 160 to 400 g/m² and the transdermal therapeutic system provides dosing for 3 to 7 days.

6. The method in accordance with claim 1, wherein said method further comprises displacing dissolved rotigotine with cutaneous water, and the transdermal therapeutic system maintains a skin permeation rate of active agent within 15% points.

7. The method in accordance with claim 1, wherein said transdermal therapeutic systems deliver the entirety of the rotigotine.

8. A method of preparing transdermal therapeutic systems comprising:
- utilizing an additive to a maintain a constant permeation rate of active agent in a transdermal therapeutic system within 20% points, said systems having an active-agent-containing layer in the form of a dried biphasic layer, which is not a hot-melt layer, having a hydrophilic inner phase and a hydrophobic outer phase comprising pressure-sensitive adhesive polysiloxane;
- the inner phase comprises the additive and active agent consisting of dissolved rotigotine;
- the additive consists of additive having a higher affinity to water than to the active agent;
- said method comprising dissolving a concentration of from 18 to 25% rotigotine for an administration period of from 3 to 7 days and
- incorporating the additive within a ratio of rotigotine to additive of 1:0.4 to 1:0.8 to maintain a constant permeation rate of the active agent during the administration period,
- wherein said additive consists of a mixture of polyvinylpyrrolidone having a K-Value of from 80 to 200 and polyvinylpyrrolidone having a K-value of 10 to 79, and said permeation rate is higher at 192 hours than 24 hours.

9. The method in accordance with claim 8, wherein the ratio is constant.

10. The method in accordance with claim 9, wherein the ratio is 1:0.44.

11. The method in accordance with claim 8, wherein said rate-maintaining additive consists of a mixture of polyvinylpyrrolidone having a K-Value of from 80 to 200, present in an amount ranging from 1:0.2 to 1:0.22, and polyvinylpyrrolidone having a K-value of 10 to 79.

12. The method in accordance with claim 8, wherein said constant permeation rate is provided for at least 24 hours after administration.

13. The method in accordance with claim 8, wherein said method further comprises selecting an amount of rotigotine sufficient for the desired administration period based upon active agent diffusion force and reducing the active agent amount based upon the cutaneous water displacement force.

14. The method in accordance with claim 8, said hydrophobic outer layer comprises pressure-sensitive adhesive(s) in ethyl acetate, and said dissolving step comprises heating at 40° C. and stirring at 500 rpm for a minimum of 60 minutes.

* * * * *

UNITED STATES PATENT AND TRADEMARK OFFICE
CERTIFICATE OF CORRECTION

| | | |
|---|---|---|
| PATENT NO. | : 11,426,359 B2 | Page 1 of 1 |
| APPLICATION NO. | : 15/312542 | |
| DATED | : August 30, 2022 | |
| INVENTOR(S) | : Emgenbroich et al. | |

It is certified that error appears in the above-identified patent and that said Letters Patent is hereby corrected as shown below:

On the Title Page

Other publications:
Line 3, delete "Office Actions in U.S. Appl. No. 16/009,613" insert --Office Actions in U.S. Appl. No. 14/975,478--

In the Claims

Claim 4, Column 20, Line 54, delete "incorporating active ingredient rotigotine-adhesive layer." insert --incorporating rotigotine into the skin-adhesive layer.--

Claim 14, Column 22, Line 21, after the phrase "with claim 8," insert --wherein--

Signed and Sealed this
Twenty-seventh Day of December, 2022

Katherine Kelly Vidal
*Director of the United States Patent and Trademark Office*